US00PP32959P2

(12) United States Plant Patent

Van Swieten

(10) Patent No.: US PP32,959 P2
(45) Date of Patent: Apr. 6, 2021

(54) *PHALAENOPSIS* ORCHID PLANT NAMED 'PHALIADIL'

(50) Latin Name: ***Phalaenopsis* hybrid**
Varietal Denomination: PHALIADIL

(71) Applicant: ANTHURA B.V., Bleiswijk (NL)

(72) Inventor: Martinus Nicolaas Gerardus Van Swieten, Utrecht (NL)

(73) Assignee: Anthura, B.V., Bleiswijk (NL)

( * ) Notice: Subject to any disclaimer, the term of this patent is extended or adjusted under 35 U.S.C. 154(b) by 0 days.

(21) Appl. No.: 17/005,602

(22) Filed: Aug. 28, 2020

(51) Int. Cl.
*A01H 6/62* (2018.01)
*A01H 5/02* (2018.01)

(52) U.S. Cl.
USPC ..... Plt./311

(58) Field of Classification Search
None
See application file for complete search history.

(56) References Cited

PUBLICATIONS

Pluto Plant Variety Database Nov. 4, 2020. p. 1.*

* cited by examiner

*Primary Examiner* — Annette H Para
(74) *Attorney, Agent, or Firm* — Jondle & Associates, P.C.

(57) ABSTRACT

A new and distinct variety of *Phalaenopsis* plant named 'PHALIADIL', particularly characterized by white flowers with greenish-yellow-white lips, short plants with relatively large flowers, leaves with lighter green margins, and is propagated by meristem tissue culture, is disclosed.

3 Drawing Sheets

Genus and species: *Phalaenopsis* hybrid.
Variety denomination: 'PHALIADIL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIADIL'.

The new *Phalaenopsis* plant is a product of a planned breeding program conducted by the inventor in Bleiswijk, the Netherlands. The objective of this breeding program was to create a new, short *Phalaenopsis* plant with relatively large, white flowers and greenish-yellow-white lips, suitable for potted plant production.

The new *Phalaenopsis* plant 'PHALIADIL' is a result of cross-pollination made by the inventor in March 2012 in Bleiswijk, the Netherlands, of the proprietary female, or seed parent, *Phalaenopsis* hybrid '01-2060' (unpatented) with the proprietary male, or pollen parent, *Phalaenopsis* hybrid '6541-01' (unpatented).

The new *Phalaenopsis* was selected by the inventor as a single plant within the progeny of the stated cross-pollination in a controlled greenhouse in Bleiswijk, the Netherlands, in January 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2373), by Applicant who obtained the subject matter disclosed directly from the inventor. 'PHALIADIL' has not been made publicly available or sold anywhere in the world prior to the effective filing date of this application with the exception of sales or disclosures made one year or less before the effective filing date of this claimed invention by Applicant who obtained 'PHALIADIL' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIADIL' as a new and distinct variety of *Phalaenopsis* plant:

1) White flowers with greenish-yellow-white lips;
2) Plant is short and has relatively large flowers; and
3) Leaves have a lighter green margin.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in July 2020. Colors in the photographs may differ from the color values cited in the detailed botanical description, which accurately describe the actual colors of the new variety.

DESCRIPTION OF THE NEW VARIETY

Figure 1:
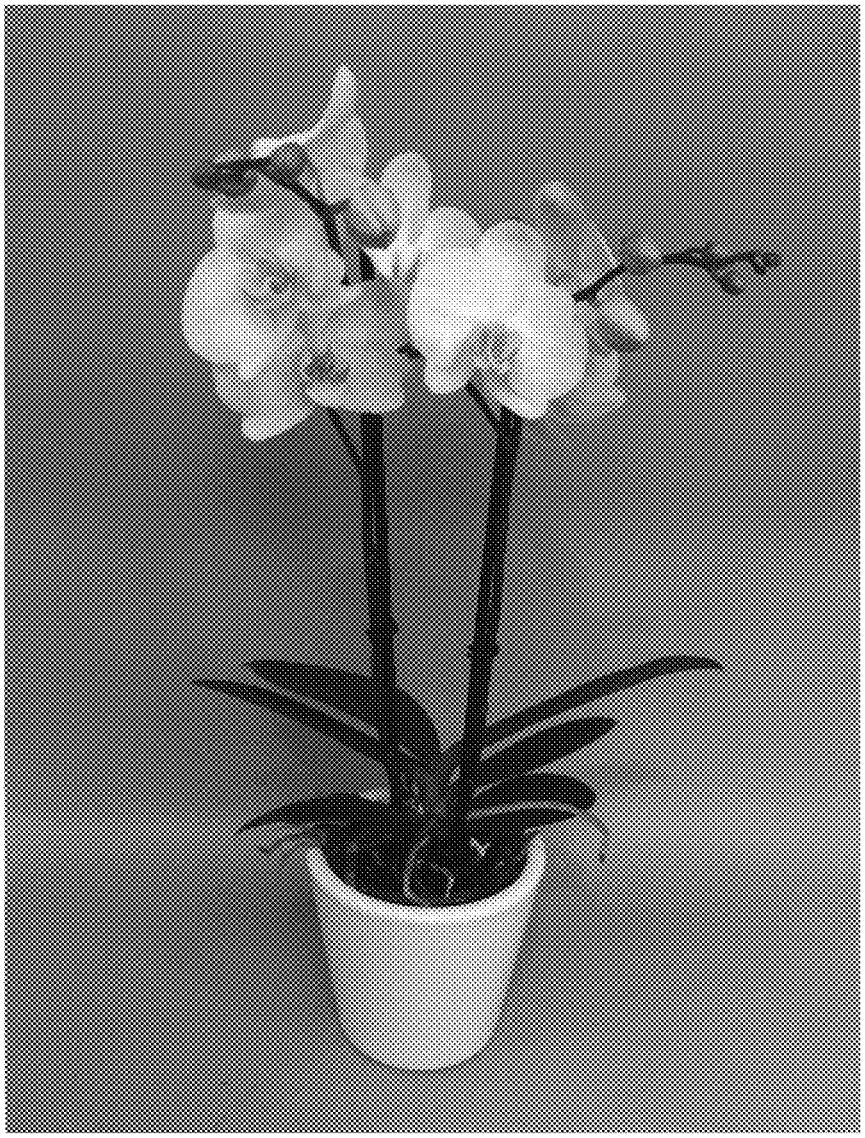
FIG. 1 shows the overall plant habit, including blooms, buds, and foliage of 'PHALIADIL'.
Figure 2:
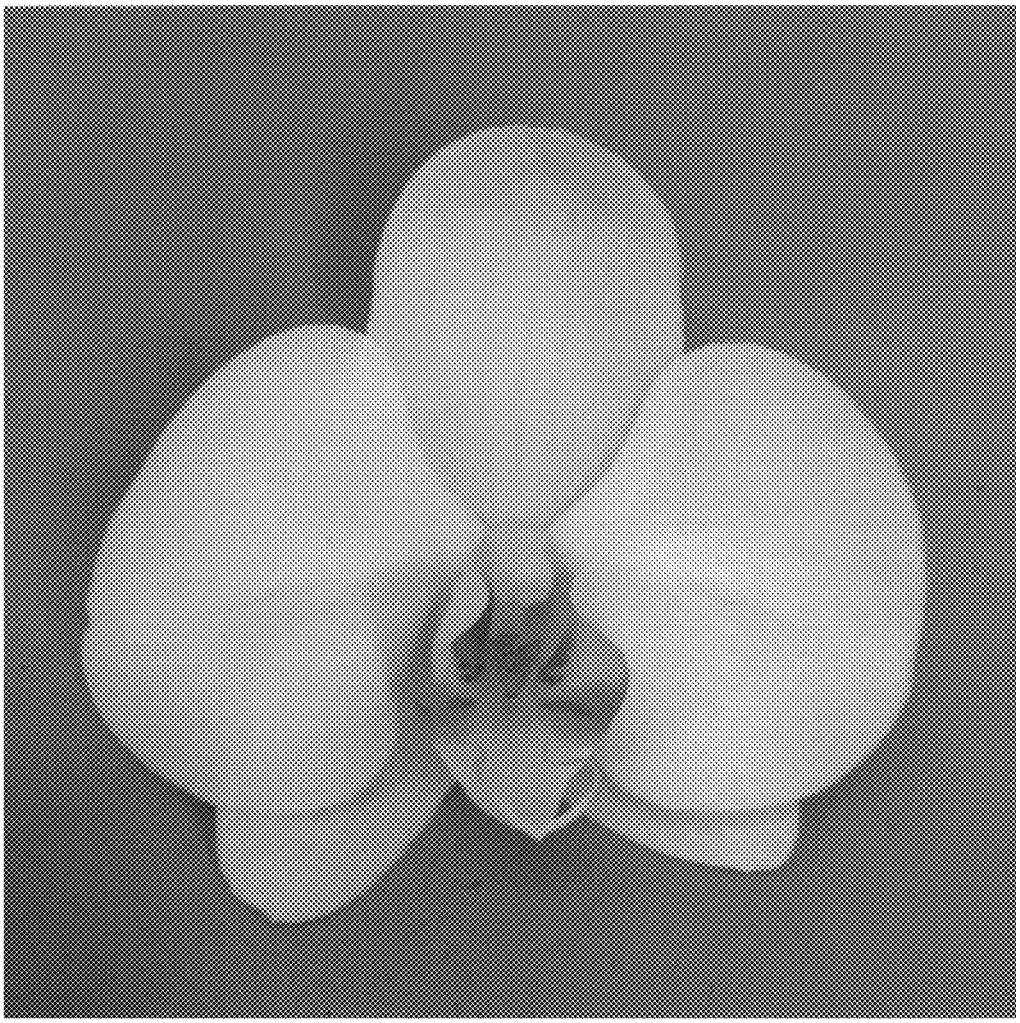
FIG. 2 shows a close-up of a flower of 'PHALIADIL'.
Figure 3:
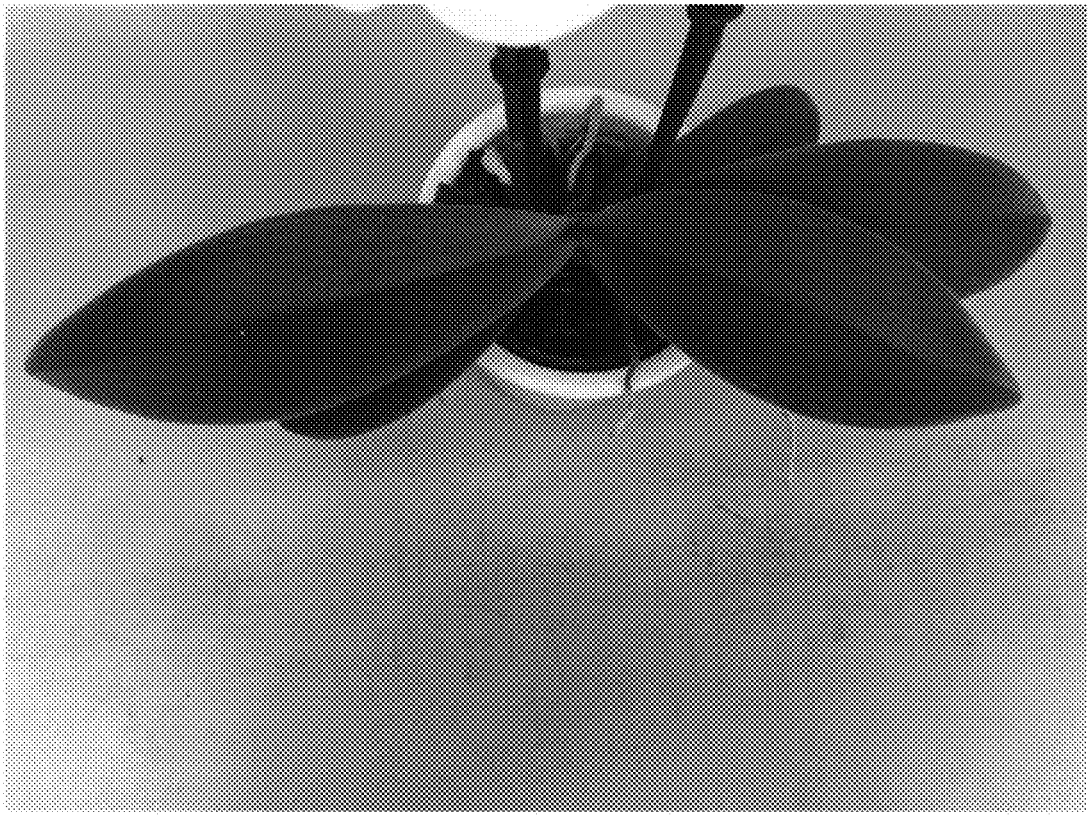
FIG. 3 shows an overhead view of the leaves of 'PHALIADIL'.

The following detailed description sets forth the distinctive characteristics of 'PHALIADIL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in July 2020 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIADIL'.

Parentage:

*Female parent*.—*Phalaenopsis* cultivar '01-2060' (unpatented).

*Male parent*.—*Phalaenopsis* cultivar '6541-01' (unpatented).

Propagation:

*Type*.—Meristem tissue culture.

Roots:

*Root description*.—Greyed-green (in between RHS 190B and 190C) colored roots with branching lateral roots having yellow-green (in between RHS 145B and N144A) colored root tips.

Plant:

*Commercial crop time to flowering*.—Following asexual propagation (in vitro), the rooted cuttings grow for 18-20 weeks. After transplantation into 9-cm pots, the plants are finished after 40 to 42 weeks.

*Growth habit of the peduncle*.—Upright to slightly pendent with raceme inflorescence.

*Height (from soil level to top of inflorescence)*.—Approximately 32.0 cm to 37.0 cm.

*Width (measured from leaf tips)*.—About 27.0 cm to 29.0 cm.

*Vigor*.—Strong.

Leaves:

*Mature leaves*.—Quantity per plant: 9 to 10 leaves are produced before flowering. Length (fully expanded): 13.0 cm to 16.0 cm. Width: 5.0 cm to 6.0 cm. Position of the broadest part of the leaf: At the middle. Shape: Oblong. Base shape: Moderately elongated. Apex: Acute unequal. Leaf blade angle with the petiole (measured from the horizontal position): Between 15 degrees and 35 degrees. Leaf margin: Entire. Color: Upper surface: Something in between RHS 146A and 147A with lighter green margin (RHS 144B). Lower surface: Something in between RHS 146B and 147B. Texture (both upper and lower surfaces): Smooth. Thickness: 2.3 mm to 2.6 mm. Variegation: Absent. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—10 to 14.

*Length*.—32.0 cm to 37.0 cm.

*Diameter*.—4.8 mm to 5.1 mm.

*Strength*.—Strong.

*Aspect*.—Upright to slightly pendent.

*Texture*.—Smooth.

*Color*.—Yellow-green (RHS 144B) with a touch of brown (something in between RHS 200B and 200C).

*Internode length*.—1.5 cm to 2.5 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 150.0 mm to 200.0 mm.

*Flowering time*.—First flowers can be expected 7 to 8 months after planting in a 9-cm pot.

*Flower*.—Height: 72.0 mm to 77.0 mm. Diameter: 80.0 mm to 85.0 mm. Depth of lip: 21.0 mm to 23.0 mm.

*Flower longevity*.—On the plant: 9 to 11 weeks.

*Flower shape*.—Flat.

*Fragrance*.—Absent.

*Flower bud*.—Average size: Medium to large. Length: 21.0 mm to 23.0 mm. Width: 16.0 mm to 18.0 mm. Shape: Egg shaped. Color: Mix of yellow-green (something in between RHS N144D and 150C).

*Petals*.—Arrangement: Open/free. Shape: Semi-circular. Apex: Slightly emarginated asymmetric. Margin: Weakly undulated. Length (from base to tip): 37.0 mm to 39.0 mm. Width: 48.0 mm to 50.0 mm. Position of the broadest part of the petal: Toward the base. Color (when fully opened): Upper surface: Basic color: White (RHS NN155C). Over color: Absent. Lower surface: Basic color: White (RHS NN155C). Over color: Absent. Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal*.—Shape: Elliptic. Apex: Emarginated symmetric; slightly cupped. Margin: Entire. Length (from base to tip): 43.0 mm to 45.0 mm. Width: 33.0 mm to 35.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Touch of light green (RHS 145D) and diluting very light purple toward the tip (RHS 76B). Number of spots and stripes on the dorsal sepals (upper surface):

None. Color of spots and stripes on the dorsal sepals (upper surface): Not applicable. Density of netting of the dorsal sepals (upper surface): None. Color of the netting: Not applicable.

*Lateral sepals*.—Shape: Ovate. Apex: Obtuse asymmetric. Margin: Entire; weakly twisted. Length (from base to tip): 48.0 mm to 50.0 mm. Width: 25.0 mm to 27.0 mm. Position of the broadest part of the lateral sepals: Toward the base. Color (when fully opened): Upper surface: Basic color: White (RHS NN155C). Over color: Absent. Lower surface: Basic color: White (RHS NN155C). Over color: Light yellow-green (something in between RHS 145C and 145D) at the base and purplish-pink midvein (RHS 186D) toward the tip. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 14.0 mm to 16.0 mm. Color of whiskers: White (RHS NN155C) at the base with yellow-green tips (RHS 154D). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated (widely wavy). Length: 18.0 mm to 20.0 mm. Width: 13.0 mm to 15.0 mm. Color: Upper surface: Greenish-yellow on one side (at the base toward the callus RHS 6A and toward the tip RHS 151B) and white (RHS NN155C) toward margin on the other side. Lower surface: Greenish-yellow on one side (at the base toward the callus RHS 6A and toward the tip RHS 151B) and white (RHS NN155C) toward margin on the other side. Number of spots and stripes on the lateral lobe (upper surface): Few stripes at the base. Color of spots and stripes on the lateral lobe (upper side): RHS 183D. Density of netting of the lateral lobe (upper surface): None. Color of the netting (upper surface): None.

*Apical lobe*.—Shape: Triangular. Margin: Entire. Length: 20.0 mm to 22.0 mm. Width: 23.0 mm to 25.0 mm. Color: Upper surface: Reddish-orange margin (RHS 178B) at the base; greenish-yellow wings (something in between RHS 6A and 151B); white (RHS NN155C) toward whiskers. Lower surface: Reddish-orange margin (RHS 178B) at the base; greenish-yellow wings (something in between RHS 6A and 151B); white (RHS NN155C) toward whiskers. Number of spots and stripes on the apical lobe (upper surface): None. Color of spots and stripes on the apical lobe (upper surface): Not applicable. Density of netting of the apical lobe (upper surface): None. Color of the netting (upper surface): None.

*Callus*.—Average size: Medium. Height: 5.0 mm to 6.0 mm. Length: 5.0 mm to 6.0 mm. Width: 3.0 mm to 4.0 mm. Color: Yellow (RHS 7A); light yellow-green (RHS 5C) on sides; dotted (RHS 178A).

Reproductive organs:

*Column*.—Length: 7.0 mm to 9.0 mm. Diameter: 5.0 mm to 6.0 mm. Color: White (RHS NN155C).

*Pollinia*.—Quantity: 2. Diameter: 0.9 mm to 1.1 mm. Color: Orange (RHS 24A).

*Ovary*.—Length: 11.0 mm to 13.0 mm. Diameter: 2.3 mm to 2.6 mm.

*Pedicel*.—Length: 31.0 mm to 33 .0 mm. Diameter: 2.7 mm to 3.0 mm. Texture: Smooth. Color: Hint of light yellow-green (something in between RHS 145A and 145B) at the base and lighter yellow-green (RHS 157C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIADIL' differs from female parent plant '01-2060' (unpatented) in that 'PHALIADIL' has slightly emarginated petal apexes, whereas '01-2060' has rounded petal apexes. Additionally, 'PHALIADIL' has smaller flowers and shorter whiskers than '01-2060'.

'PHALIADIL' differs from male parent plant '6541-01' (unpatented) in that 'PHALIADIL' has smaller flowers and shorter whiskers than '6541-01'.

'PHALIADIL' is most similar to the commercial *Phalaenopsis* plants named 'PHALGREKK' (U.S. Plant patent application Ser. No. 16/873,358) and 'PHALBAPAK' (U.S. Plant Pat. No. 27,508). 'PHALIADIL' differs from the commercial variety 'PHALGREKK' in that 'PHALIADIL' has slightly emarginated petal apexes, whereas 'PHALGREKK' has obtuse petal apexes. Additionally, 'PHALIADIL' has larger flowers, longer leaves, longer whiskers, and more leaves per plant than 'PHALGREKK'.

'PHALIADIL' differs from the commercial variety 'PHALBAPAK' in that 'PHALIADIL' has emarginated and slightly cupped dorsal sepal apexes and whiskers that are white at the base with yellow-green tips, whereas 'PHALBAPAK' has obtuse dorsal sepal apexes and whiskers that are white.

I claim:

1. A new and distinct variety of *Phalaenopsis* plant named 'PHALIADIL', substantially as described and illustrated herein.

* * * * *